United States Patent [19]
Engel

[11] Patent Number: 5,889,192
[45] Date of Patent: *Mar. 30, 1999

[54] METHOD FOR TEMPERATURE COMPENSATION OF MEASURED VALUES OF A TURBIDITY SENSOR IN AN AUTOMATIC WASHING MACHINE OR DISWASHER

[75] Inventor: Christian Engel, Berlin, Germany

[73] Assignee: BSH Bosch und Siemens Hausgeraete GmbH, Munich, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 877,101

[22] Filed: Jun. 17, 1997

Related U.S. Application Data

[63] Continuation of Ser. No. 662,353, Jun. 12, 1996, abandoned.

[30] Foreign Application Priority Data

Jun. 12, 1995 [DE] Germany .................. 195 21 326.2

[51] Int. Cl.[6] .................................................. D06F 33/02
[52] U.S. Cl. ............................................ 73/1.02; 68/12.03
[58] Field of Search .................. 73/1 R, 1 G, 865.5, 73/1.02; 356/442; 68/12.02, 12.03; 134/18, 57 D, 58 D, 137, 25.02

[56] References Cited

U.S. PATENT DOCUMENTS

| | | |
|---|---|---|
| 3,586,862 | 6/1971 | Topol . |
| 3,665,201 | 5/1972 | Shea et al. . |
| 5,477,576 | 12/1995 | Berkcan ................................ 68/12.03 |
| 5,555,583 | 9/1996 | Berkcan ................................ 68/12.02 |

*Primary Examiner*—Robert Raevis
*Attorney, Agent, or Firm*—Herbert L. Lerner; Laurence A. Greenberg

[57] ABSTRACT

A turbidity sensor is built in at a location being reachable by washing fluid in an automatic washing machine having a microprocessor for process control, a light transmitter and a light receiver for transmitting light through the washing fluid in a measurement path. A method for temperature compensation of measured values of the turbidity sensor includes calculating a temperature coefficient of the turbidity sensor for each operating point and storing the temperature coefficient in memory as a correction value in software for evaluating measurement results of the turbidity sensor. A respective measurement result is corrected by using the temperature coefficient as a function of a temperature being present and measured at the turbidity sensor.

1 Claim, 4 Drawing Sheets

METHOD FOR TEMPERATURE COMPENSATION OF MEASURED VALUES OF A TURBIDITY SENSOR IN AN AUTOMATIC WASHING MACHINE OR DISWASHER

This application is a continuation of application Ser. No. 08/662,353, filed on Jun. 12, 1996, now abandoned.

BACKGROUND OF THE INVENTION

FIELD OF THE INVENTION

The invention relates to a method for temperature compensation of measured values of a turbidity sensor which is built in at some location that is reachable by washing fluid in a water-carrying household appliance, preferably an automatic washing machine or dishwasher, having process control using a microprocessor and containing a light transmitter and a light receiver for transmitting light through the washing fluid located within a measurement path.

The turbidity of the washing fluid can be detected as a process parameter and used to optimize the rinse cycle through the use of a turbidity sensor in the washing machine. Since the turbidity sensor is located in the vicinity of the washing fluid, there is a thermal coupling between the turbidity sensor and the washing fluid. The temperature of the washing fluid may fluctuate in normal operation between about 10° and 95°, so that the turbidity sensor is likewise exposed to severe temperature fluctuations.

The turbidity sensor functions according to an optical method and includes a transmitter (such as an LED), which transmits light in the near infrared range, and an optical receiver (phototransistor or photodiode or photoresistor), which converts the optical infrared signal into a proportional electrical signal. However, the transmitter (infrared LED, for instance) and the receiver being used (phototransistor, for instance) are highly temperature-dependent in their electrooptical properties. Without suitable temperature compensation, temperature fluctuations would be interpreted as fluctuations in the turbidity value and would lead to incorrect results in the evaluation of the signal. A temperature compensation of the turbidity sensor is therefore necessary in all appliances in which the turbidity sensor is exposed to major temperature fluctuations, such as in washing machines or dishwashers.

A washing machine with a device for measuring the dirtiness of the washing fluid is known from Published European Patent Application 0 393 311 A1. That device likewise uses an electrooptical turbidity sensor, which is to be calibrated at the beginning of a process that includes a plurality of turbidity measurements. That calibration relates to a reference value for the turbidity which is intended to be equivalent to a measured value definition of zero. To that end, before the measurements begin, the turbidity sensor is exposed to pure tap water or air, and the measurement value thus obtained is defined as zero. However, the known device does not take into account the fact that the ambient temperature of the turbidity sensor can fluctuate sharply and has a considerable influence on the magnitude of the measured turbidity value.

If a combination of a phototransistor and an IR LED is used for the turbidity measurement, then the temperature coefficients of the two components are superimposed on one another, and a total coefficient is obtained for the turbidity sensor. That is also true when similar components are used.

The total temperature coefficient is composed of many influencing variables, which are listed herein as examples for the combination of an IR LED and a phototransistor:

The radiation of the transmitter shifts with increasing temperature to higher wavelengths. The coupling factor between the transmitter and the receiver thus varies as well.

The radiation out of the transmitter drops with decreasing temperature. As a result, the measurement current in the phototransistor drops by the factor according to which the light intensity decreases.

Upon heating up of the IR LED, the on-state voltage drops by approximately 2 mV/K, and as a result if the on-state current remains the same the electrical output or performance drops. The light intensity drops even further as a result.

At a high temperature, the IR LED ages faster, and the consequence is a decreasing light intensity.

The spectral sensitivity of the phototransistor varies with the temperature, resulting in a variation in the coupling factor between the phototransistor and the IR LED.

The current gain factor of the phototransistor increases with a rising temperature. As a result, the measurement current in the phototransistor rises while the light intensity is constant.

The dark current of the phototransistor rises with increasing temperature, resulting in a general raising of the measurement current, regardless of the light intensity.

The phototransistor ages faster at a high temperature, leading to a change in the electrooptical parameters.

The index of refraction of the water in the measurement path varies with the temperature. As a result, the photooptical parameters of the beam path between the transmitter and the receiver vary, which in turn affects the coupling factor.

It is apparent from the many parameters that are dependent on the temperature and have an influence on the measurement current, that one cannot compensate for every influencing variable individually. The turbidity sensor must therefore be considered as an overall system, having parameters which must be determined by trial and error. That is particularly true for the temperature coefficients of the electronic components of the turbidity sensor, because they are very strongly expressed in the measurement result.

In experiments it has been found to be particularly problematic that the ascertained temperature coefficient is also dependent on the particular operating point. That is true both for the receiver (phototransistor, for instance) and the transmitter (IR LED, for instance). In the phototransistor, the temperature coefficient is dependent on the collector-to-emitter voltage, and in the IR LED it is dependent on the on-state current. If the on-state current of the IR LED is constant, then while the temperature coefficient of the IR LED does not vary, nevertheless the collector-to-emitter voltage of the phototransistor and thus its temperature coefficient vary as a function of the turbidity. In the temperature compensation, one can therefore not expect a constant compensation factor but instead must adapt the compensation factor dynamically.

The temperature coefficient of a turbidity sensor, over the temperature range applicable to washing fluids, when the so-called transmitted light method is used, is discussed below with reference to FIG. 1.

The same measurement without making the measurement path turbid, is discussed below with regard to FIG. 2.

Without suitable compensation, such temperature-dictated signal drifts would make the turbidity measurement so markedly wrong that a conclusive measurement of turbidity would no longer be possible.

SUMMARY OF THE INVENTION

It is accordingly an object of the invention to provide a method for temperature compensation of measured values of a turbidity sensor in an automatic washing machine or dishwasher, which overcomes the herein afore-mentioned disadvantages of the heretofore-known methods of this general type and which obtains correct turbidity measurement values for all temperatures in a relevant range and for all turbidity variants.

Temperature compensation of the sensor is admittedly absolutely necessary. As can be seen from the examples, however, no universally valid temperature coefficient can be given.

With the foregoing and other objects in view there is provided, in accordance with the invention, a method for temperature compensation of measured values of a turbidity sensor being built in at a location reachable by washing fluid in an automatic washing machine having a microprocessor for process control, a light transmitter and a light receiver for transmitting light through the washing fluid in a measurement path, which comprises calculating a temperature coefficient of the turbidity sensor for each operating point and storing the temperature coefficient in memory as a correction value in software for evaluating measurement results of the turbidity sensor; and correcting a respective measurement result by using the temperature coefficient as a function of a temperature being present and measured at the turbidity sensor.

Due to the drift in the operating point as a function of the turbidity, the temperature coefficient in fact varies as well. Temperature compensation is therefore possible only by dynamically adapting the compensation according to the invention to the given operating point.

In accordance with another mode of the invention, first a measurement result is recorded at the turbidity sensor, and from it the operating point of the turbidity sensor is ascertained. Moreover, after the immediately ensuing or simultaneous measurement of the ambient temperature of the turbidity sensor, taking into account the measured value of the ambient temperature and of the operating point, the correction value is calculated and added to the measurement result.

The compensation would then be carried out in accordance with the following scheme:

1. Measurement of the turbidity signal.
2. Ascertainment of the operating point.
3. Measurement of the temperature at the turbidity sensor.
4. Calculation of the correction value for the ascertained operating point and the measured temperature.
5. Adding the correction value to the measurement value, to obtain the compensated turbidity measurement value.

A dynamic temperature compensation can therefore best, and especially economically, be achieved by software controlled evaluation of the turbidity signal. The temperature coefficient is ascertained and integrated with the evaluation software for every possible operating point of the sensor. In terms of hardware, the sensor is supplemented with a temperature probe, so that the associated temperature can be ascertained for every operating point of the sensor.

In accordance with a concomitant mode of the invention, first the ambient temperature of the turbidity sensor is measured and from it the operating point of the turbidity sensor is ascertained. Furthermore, a compensation value, by which the input variable of the turbidity sensor is to be varied for the ensuing turbidity measurement, is calculated from the deviation of the ascertained operating point from the typical operating point of the turbidity sensor.

This alternative method can accordingly proceed as follows:

1. Measurement of the temperature at the turbidity sensor.
2. Ascertainment of the operating point.
3. Calculation of a compensation value by which the transmitting current of the transmitter (IR LED, for instance) is to be varied so that the influence of temperature can be compensated for.
4. Addition of the compensation value to the former transmitting current and establishment of the new transmitting current.
5. Measurement of the corrected turbidity signal.

Through the use of the invention it is possible to determine the turbidity of liquids that are subject to temperature fluctuations during the measurement. The measured values obtained are free of errors from temperature influences. Through the use of the temperature monitoring, the components can simultaneously be protected against destruction from excessively high operating temperatures. The temperature probe can moreover be used to monitor the temperature of the washing fluid. Therefore, no separate temperature probe is intrinsically necessary for the temperature compensation of the turbidity signal.

Other features which are considered as characteristic for the invention are set forth in the appended claims.

Although the invention is illustrated and described herein as embodied in a method for temperature compensation of measured values of a turbidity sensor in an automatic washing machine or dishwasher, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
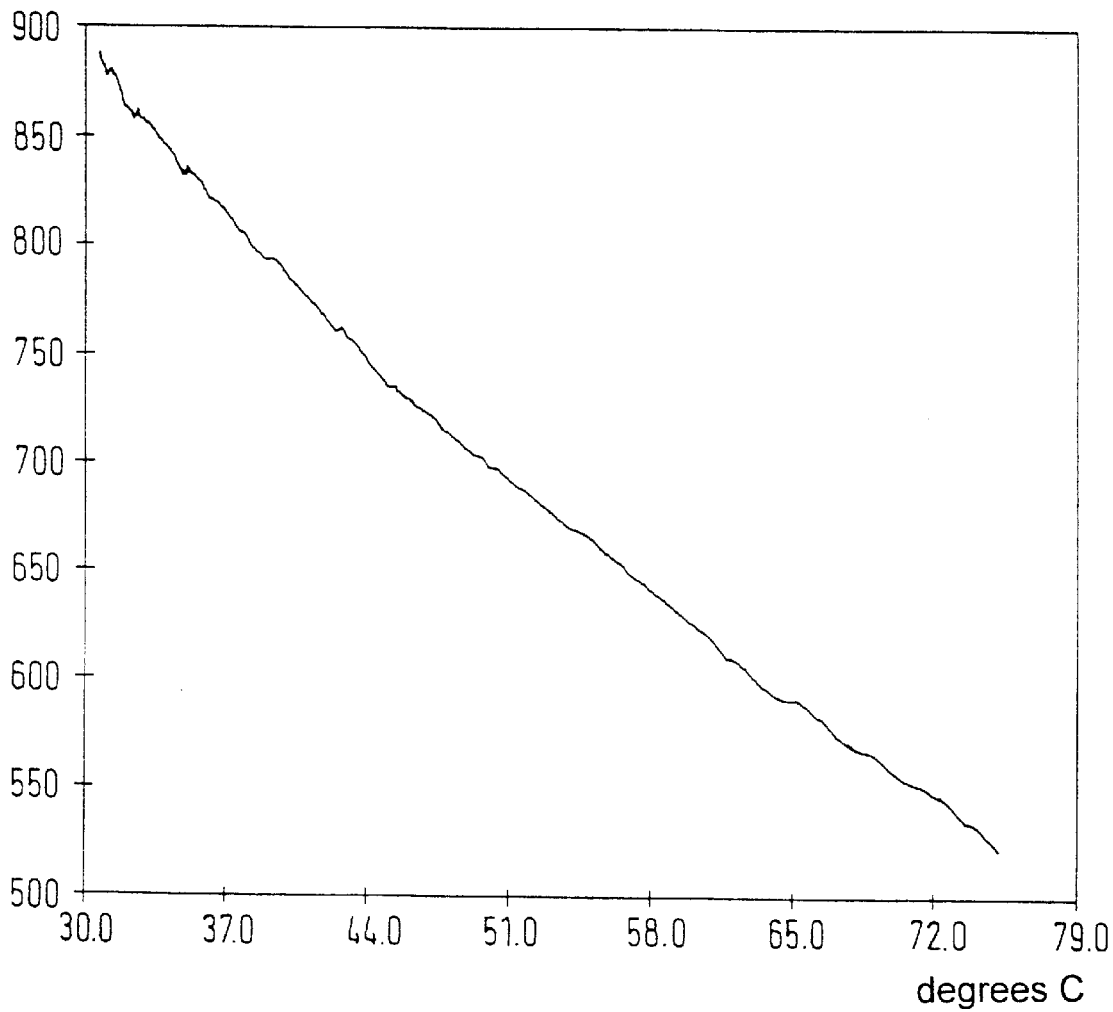
FIG. 1 is a diagram showing a course of a temperature coefficient of a turbidity sensor, over a temperature range applicable to washing fluids, in an employment of a so called transmitted light method.

Referring now to the figures of the drawings in detail and first, particularly, to FIG. 1 thereof, there is seen a temperature coefficient of a turbidity sensor which is plotted against a temperature range that is applicable to washing fluids, when a so-called transmitted light method is used. The fluid is used in an automatic washing machine, which is understood to include both a washing machine for clothes and a washing machine for dishes. An SFH484 IR LED was Used as a transmitter, and an SFH309F phototransistor was used as a receiver. A transmitting current of the LED was 5 mA in the measurement, and artificial turbidity was created through the use of a plastic strip. The sensor was located in an air-conditioning cabinet during the measurement. Measurement was carried out during the cooling down phase. The result of the measurement was a temperature coefficient of −6.6 mV/K or −0.95%/K.

Figure 2:
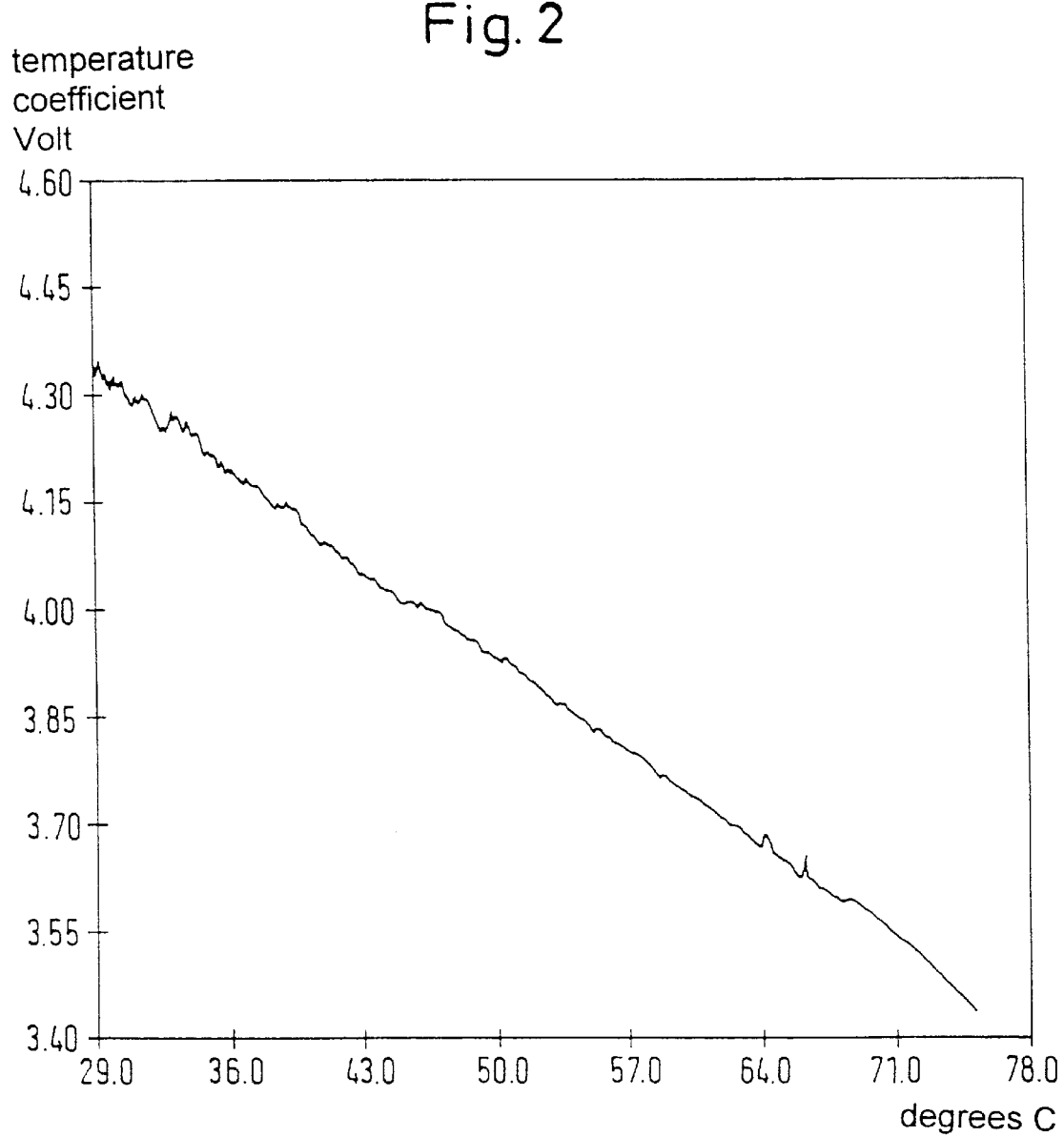
FIG. 2 is a diagram showing a course without turbidity of a measurement path and otherwise with the same experimental conditions as in FIG. 1.

FIG. 2 shows the same measurement without making the measurement path turbid. The experimental conditions are otherwise the same as in the previous measurement. The temperature coefficient ascertained in that measurement is −20.4 mV/K or −0.52%/K. Thus in the second measurement the temperature coefficient was only about half as great as in the measurement with simulated turbidity. The transmitting current of the IR LEDs was identical in both measurements, but not the operating point, since a lower collector current is generated in the phototransistor as a result of the simulated turbidity than without turbidity. However, as a result of the low collector current, the collector-to-emitter voltage rises, since a lower voltage drops at the measurement resistor.

The same is true for the IR LED, in which the transmitted infrared light becomes weaker with rising temperature. In IR LEDs, the temperature coefficient as a rule is between −0.7% and −0.5%/K, depending on the semiconductor material being used.

Although the temperature coefficients of the phototransistor and the IR LED act counter to one another, they do not cancel one another out. The resultant coefficient must accordingly be compensated for in every case.

The temperature range to which the turbidity sensor is exposed in the worst case is about 85° Kelvin, and specifically ranges from about 10° to about 95° Celsius. On the assumption that the temperature coefficient would be 0.95%/K, the result is a drift in the output signal of 80.75%, without any change whatever in the turbidity. In the case of the experiment without turbidity, with a temperature coefficient of 0.52%/K, there is still a drift of 44.2% under those peripheral conditions. Although static temperature compensation is also possible, nevertheless it then applies to only a certain operating point, which greatly restricts the operating range of the sensor.

As mentioned above, without suitable compensation, such temperature-dictated signal drifts would make the turbidity measurement so markedly wrong that a conclusive measurement of turbidity would no longer be possible.

In accordance with the invention, an NTC resistor, PTC resistor, or thermocouple may, for instance, be used as the temperature sensor. Possibilities for the light source are an LED, laser diode, incandescent lamp, neon lamp, fluorescent tube or similar light sources. Suitable receiving elements are a phototransistor, photodiode, photoresistor, photo element, photocell or similar receiving element.

Figure 3:
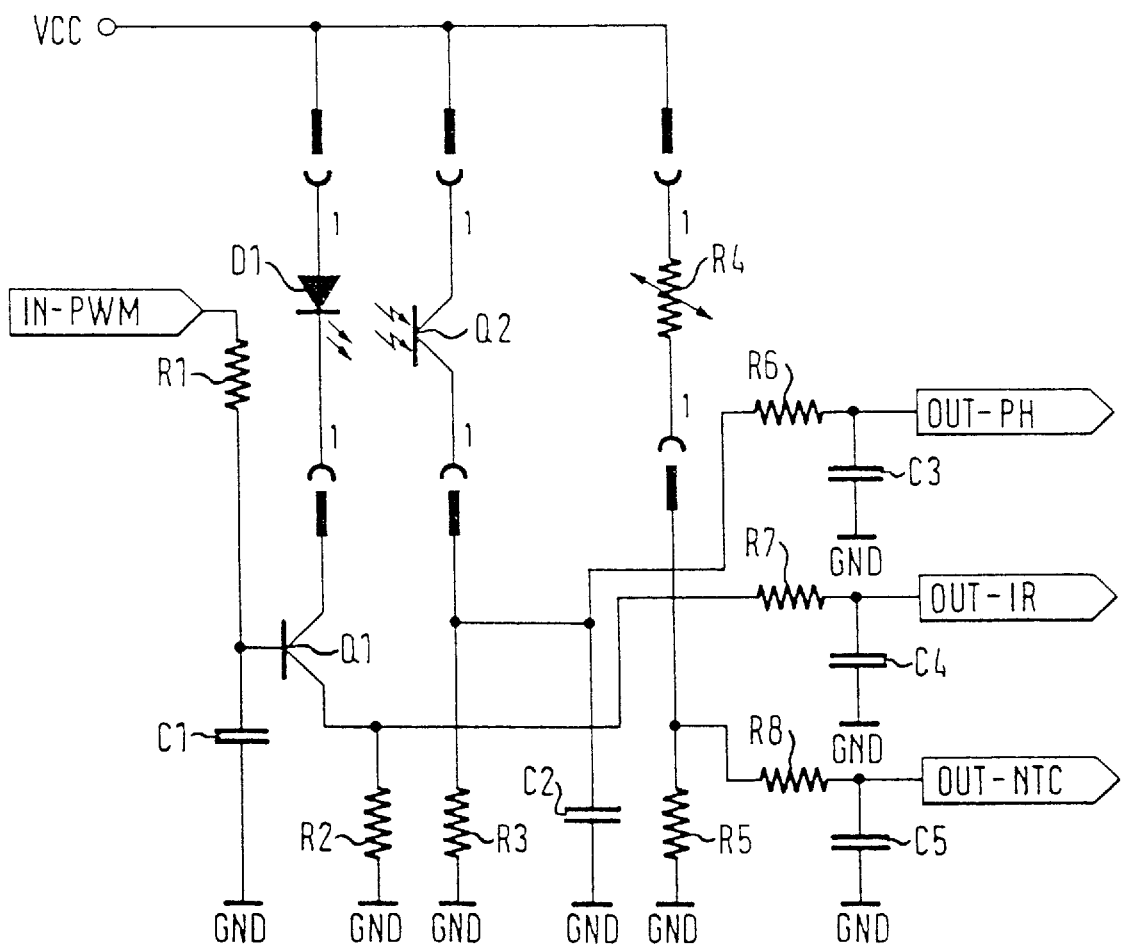
FIG. 3 is a schematic circuit diagram for a turbidity sensor with temperature compensation according to the invention.

FIG. 3 shows a circuit for a turbidity sensor with temperature compensation according to the invention. The turbidity sensor substantially includes an IR LED D1, a phototransistor Q2 and a temperature probe (NTC or PTC resistor) R4. A transmitter is formed by triggering of the IR LED through the use of a pulse width modulated signal (PWM signal), which is present at a resistor R1. The resistor R1 together with a capacitor C1 forms a low-pass filter, having a cut-off frequency which must be substantially higher than the frequency of the PWM signal. Thus, on the basis of the PWM signal, an analog voltage is generated which is proportional to the duty cycle of the PWM signal. This voltage is present at the base of a transistor Q1, and thus the voltage at a resistor R2 is also defined.

The transistor Q1 in this case operates as a voltage-controlled current source for the IR LED located in the collector branch. The current through the IR LED is equal to the collector current, which is approximately equivalent to the emitter current (ignoring the base current which by comparison is very low). The emitter current is defined by the voltage drop at the resistor R2. This voltage drop is carried through a low-pass filter including a resistor R7 and a capacitor C4 to the outside as an output signal OUT-IR and is proportional to the current through the IR LED.

On the receiver side, the phototransistor Q2 is connected in series with a resistor R3, in order to convert the photo-current of the transistor into a proportional voltage that drops at the resistor R3. A capacitor C2 then smoothes the signal before it is made available as an output signal OUT-PH through a low-pass filter including a resistor R6 and a capacitor C3.

The temperature compensation requires a temperature measurement through the use of a temperature sensor. The resistor R4 and a resistor R5 form a voltage divider having a divider voltage which is temperature-dependent, since the resistor R4 is an NTC resistor. This circuit portion serves to measure the temperature of the turbidity sensor which, through the use of an evaluation, becomes a signal OUT-NTC that is taken to the outside through a low-pass filter including a resistor R8 and a capacitor C5.

Figure 4:
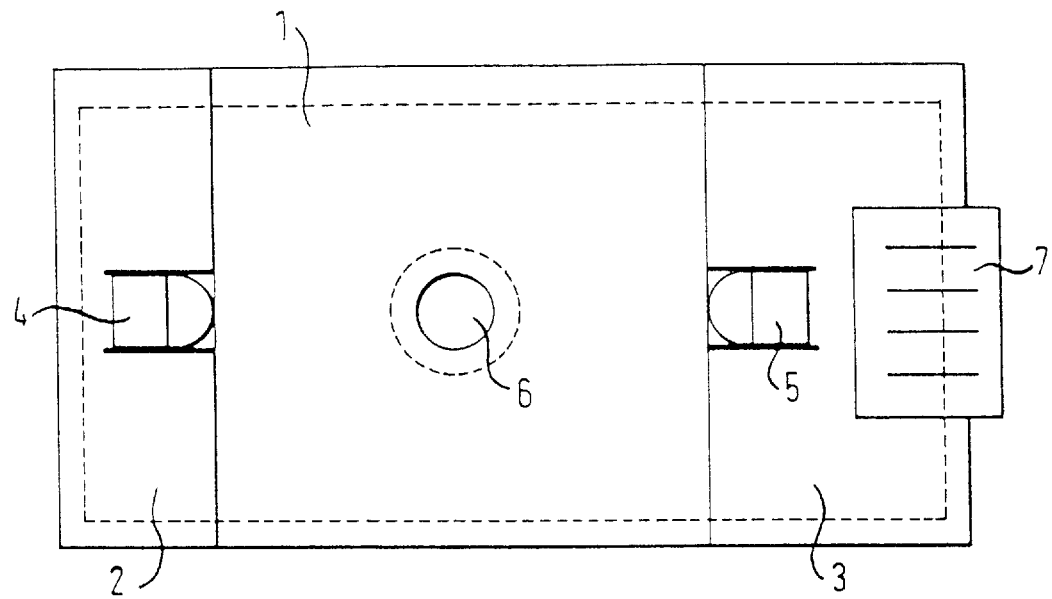
FIG. 4 is a top-plan view of an exemplary embodiment of a three-dimensional structure of a turbidity sensor with a temperature sensor compensating for temperature error.
Figure 5:
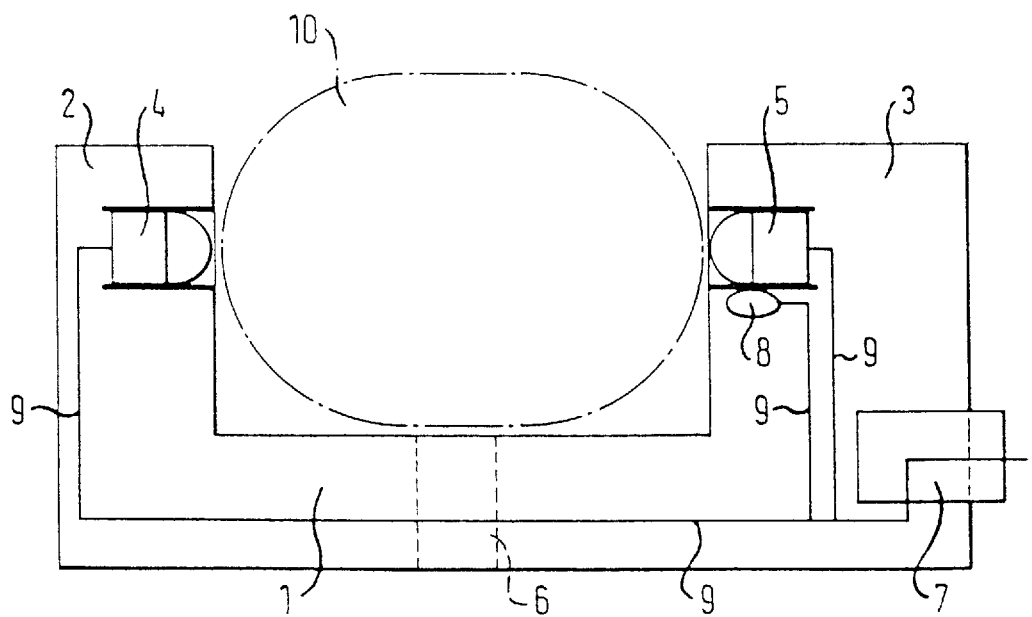
FIG. 5 is a side-elevational view of the turbidity sensor of FIG. 4.

An important factor in the securing of the temperature probe is a good thermal contact between one of the sensor components and the temperature probe. FIGS. 4 and 5 show one possible version of the turbidity sensor with temperature compensation. In this version, a printed circuit board 1 serves as a bridge for two substrates 2 and 3, of which one substrate 2 carries a phototransistor 4 and the other substrate 3 carries an infrared light emitting diode 5 (IR LED). This apparatus can be secured through the use of a hole 6 in a base, such as a non-illustrated crossbar for retaining a transparent portion 10 of a line that carries liquid. The printed circuit board 1 also carries a plug connection well 7 for an external electrical connection of the apparatus. The IR LED 5 transmits light through the washing fluid located within a measurement path in the line 10 to the phototransistor 4. An NTC resistor 8 is also mounted in the substrate 3 as a temperature probe that is thermally coupled with the LED 5 and is likewise electrically connected by its own schematically illustrated lines 9 to the printed circuit board 1.

I claim:

1. A method for temperature compensation of measured values of a turbidity sensor being built in at a location reachable by washing fluid in an automatic washing machine having a microprocessor for process control, a light transmitter and a light receiver for transmitting light through the washing fluid in a measurement path, which comprises:

calculating a plurality of temperature coefficients of the turbidity sensor for a plurality of operating points and storing the plurality of temperature coefficients in a memory as correction values;

measuring an ambient temperature at the turbidity sensor and ascertaining a current operating point of the turbidity sensor from the ambient temperature; and calculating a compensation value for varying an input variable of the turbidity sensor from a deviation of the current operating point from an initial operating point of the turbidity sensor; and correcting the input variable of the turbidity sensor with the compensation value.

* * * * *